US006585760B1

(12) United States Patent
Fogarty

(10) Patent No.: US 6,585,760 B1
(45) Date of Patent: Jul. 1, 2003

(54) AV FISTULA AND FUNCTION ENHANCING METHOD

(75) Inventor: Thomas J. Fogarty, Portola Valley, CA (US)

(73) Assignee: Vascular Architects, Inc, San Jose, CA (US)

( * ) Notice: Subject to any disclaimer, the term of this patent is extended or adjusted under 35 U.S.C. 154(b) by 279 days.

(21) Appl. No.: 09/608,734

(22) Filed: Jun. 30, 2000

(51) Int. Cl.$^7$ ................................................. A61F 2/06
(52) U.S. Cl. ...................... 623/1.22; 623/1.13; 623/1.16
(58) Field of Search ............................... 623/1.1, 1.13, 623/1.14, 1.22, 1.44, 1.45, 1.46, 1.16; 128/898

(56) References Cited

U.S. PATENT DOCUMENTS

| | | | |
|---|---|---|---|
| 4,760,849 A | | 8/1988 | Kropf .......................... 128/341 |
| 5,123,917 A | * | 6/1992 | Lee ............................. 623/1.1 |
| 5,147,370 A | | 9/1992 | McNamara et al. ......... 606/108 |
| 5,282,823 A | | 2/1994 | Schwartz et al. |
| 5,639,278 A | * | 6/1997 | Dereume et al. ............. 623/1.1 |
| 5,683,451 A | | 11/1997 | Lenker et al. .................. 623/1 |
| 5,824,053 A | | 10/1998 | Khosravi et al. ............... 623/1 |
| 5,824,054 A | * | 10/1998 | Khosravi et al. ............. 623/1.1 |
| 5,866,217 A | * | 2/1999 | Stenoien et al. ............. 623/1.1 |
| 6,090,134 A | | 7/2000 | Tu et al. |
| 6,241,691 B1 | * | 6/2001 | Ferrera et al. ............. 623/1.22 |
| 6,264,684 B1 | * | 7/2001 | Banas et al. ................ 623/1.13 |
| 6,355,055 B1 | * | 3/2002 | Waksman et al. .......... 623/1.13 |

FOREIGN PATENT DOCUMENTS

WO    WO 97/40755    11/1997

OTHER PUBLICATIONS

D. Maass, CH. L. Zollikofer, F. Largiader, and A. Senning, "Radiological Follow–up of Transluminally Inserted Vascular Endoprostheses: An Experimental Study Using Expanding Spirals," Radiology, 1984, vol. 152, No. 3, pp. 659–663.

Aruny et al., "Quality Improvement Guidelines for Percutaneous Management of the Thrombosed or Dysfunctional Dialysis Access," *JVIR*, 10:491–498 (1999).

Coulson et al., "A Combination of the Elephant Trunk Anastomosis Technique and Vascular Clips for Dialysis Grafts," *Surgical Rounds*, pp. 596–608 (11/99).

Gray et al., "Reporting Standards for Percutaneous Interventions in Dialysis Access," *JVIR*, 10(10):1405–1415 (1999).

Kohler et al., "Dialysis access failure: A sheep model of rapid stenosis," *J. Vasc. Surg.*, 30:744–751 (1999).

Kohler, Ted R., "Intimal Hyperplasia—Endothelial Cell Biology," from the Seventh Biannual Symposium on Dialysis Access, Vascular Access for Hemodialysis VII, pp. 1–2 (May 2000).

Martin et al., "Prophylactic Angioplasty Reduces Thrombosis in Virgin ePTFE Arteriovenous Dialysis Grafts with Greater than 50% Stenosis: Subset Analysis of a Prospectively Randomized Study," *JVIR*, 10:389–396 (1999).

Polo, Jose R., "The State of the Art of Surgical Treatment for Failing Grafts," from the Seventh Biannual Symposium on Dialysis Access, Vascular Access for Hemodialysis VII, pp. 8–9 (May 2000).

Vesely, Thomas M., "the State of the Art of Radiologic Intervention," from the Seventh Biannual Symposium on Dialysis Access, Vascular Access for Hemodialysis VII, pp. 4–7 (May 2000).

* cited by examiner

*Primary Examiner*—Julian W. Woo
(74) *Attorney, Agent, or Firm*—James F. Hann; Haynes Beffel & Wolfeld LLP

(57) ABSTRACT

A coiled stent graft (10) is positionable within an AV fistula (4) and optionally into one or both of the artery (9) and the vein (6) to help reduce or eliminate blockages within the blood vessel at the junction (8) between the AV fistula and the blood vessel.

9 Claims, 2 Drawing Sheets

AV FISTULA AND FUNCTION ENHANCING METHOD

CROSS-REFERENCES TO RELATED APPLICATIONS

This application is related to: U.S. patent application Ser. No. 09/400,952 filed Sep. 22, 1999, now U.S. Pat. No. 6,238,430, entitled Catheter Assembly with Controlled Release Endoluminal Prosthesis; U.S. patent application Ser. No. 09/258,542 filed Feb. 26, 1999, now U.S. Pat. No. 6,248,122, entitled Catheter With Controlled Release Endoluminal Prosthesis.

BACKGROUND OF THE INVENTION

A fistula is an abnormal passage typically between two organs, such as an artery and a vein. An arterio-venous (AV) fistula is a natural or an artificial graft, typically made of ePTFE (expanded PTFE), between a vein and an artery. An AV fistula, as used herein, also includes naturally-occurring native tissue tubular connections between a vein and an artery. AV fistulas are often used to provide multiple needle access sites for hemodialysis. The AV fistula also helps to increase blood flow through the vein to accommodate the flow rate of blood needed for hemodialysis.

One problem associated with AV fistulas is the progressive narrowing of the AV fistula at the junction with the vein. Such obstructions occur when vascular muscle cells begin growing inwardly causing, for example, thrombosis within the AV fistula. When the thrombus becomes sufficiently large, blood flow decreases and the AV fistula ceases to be effective. It has been found that graft patency after six months is only 66% and that graft failure occurs, on the average, after 18 months.

Improved graft patency has been achieved by the use of vascular clips instead of suturing the AV fistula to the vein. Variations in the angle of implantation have also been shown to affect AV fistula patency. The use of a short length of a PTFE graft has been inserted in the vein to improve patency. (A. S. Coulson, et al., A Combination of the Elephant Trunk Anastomosis Technique and Vascular Clips for Dialysis Grafts, Surgical Rounds, 596–608, November 1999.) Also, a PTFE bypass graft to a proximal dilated vein has been used in response to the occurrence of graft-vein stenosis. (Polo, J. R., The State of the Art of Surgical Treatment for Failing Grafts, The Seventh Biannual Symposium on Dialysis Access—Vascular Access for Hemodialysis VII, pp.8–9, May 2000.) Balloon angioplasty and endovascular stents may be used to treat stenosis in AV fistulas (J. E. Aruny, et al., Quality Improvement Guidelines for Percutaneous Management of the Thrombosed on Dysfunctional Dialysis Access, JVIR, 10:491–498, April 1999.) However, there still exists the need to stop, or at least slow, the obstruction of the AV fistula to prolong the patency of the graft.

SUMMARY OF THE INVENTION

The present invention is directed to an AV fistula and a method for enhancing the function of an AV fistula by helping to prevent or at least retard the obstruction of the AV fistula at either or both the arterial and venous sides of the fistula.

A first aspect of the invention is directed to an AV fistula function enhancing method including selecting an endoluminal prosthesis including a coiled body and a graft material covering at least part of the coiled body to create a coiled stent graft The stent graft is placed within the AV fistula and optionally within at least one blood vessel to which the AV fistula is connected. The use of the stent graft helps to prevent, or at least retard, the obstruction of the AV fistula by eliminating, or at least reducing, the accumulation of matter in the AV fistula.

Another aspect of the invention is directed to an AV fistula assembly, including an AV fistula having a tubular body and a coiled stent graft housable at least partially within the AV fistula and at least one of the venous and arterial ends.

The turns of the stent graft at the junction may be spaced apart from one another so to insubstantially or partly hinder fluid flow along the vein. The turns of the stent graft may also be such as to effectively block fluid flow along the vein.

Other features and advantages of the invention will appear from the following description in which the preferred embodiments have been set forth in detail in conjunction with the accompanying drawings.

DESCRIPTION OF THE SPECIFIC EMBODIMENTS

Figure 1:
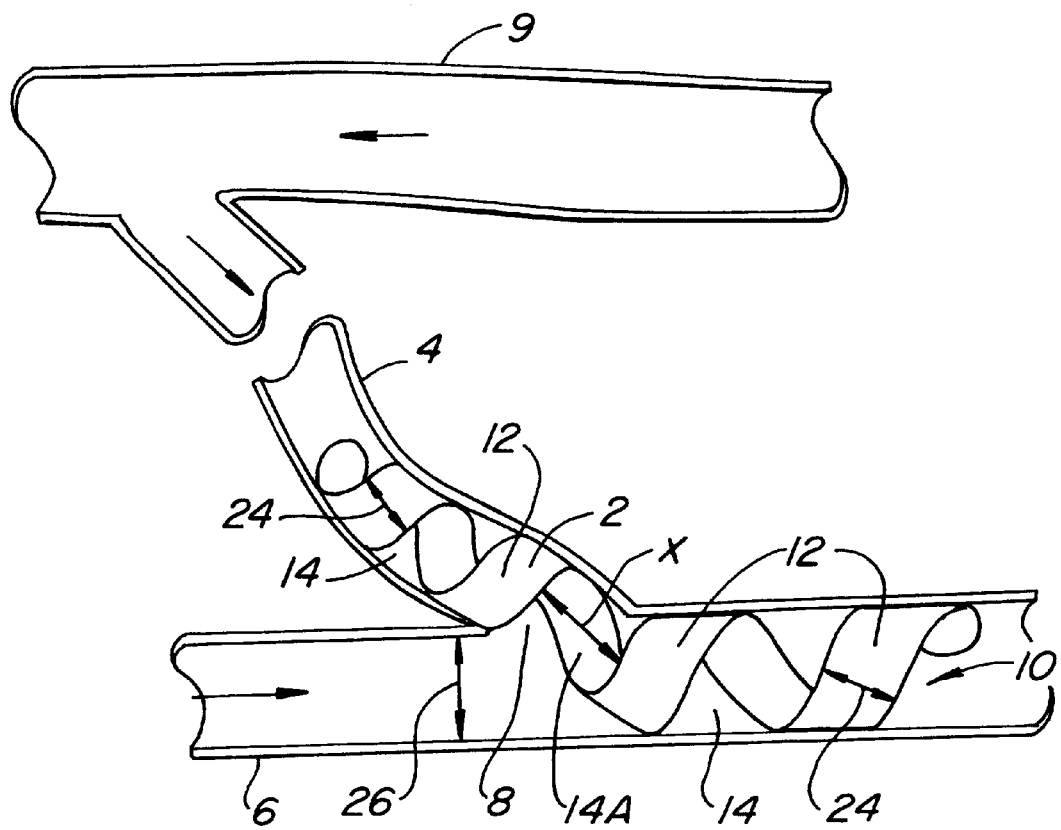
FIG. 1 is a side, partial cross-section view illustrating the venous end of an AV fistula with a stent graft extending from the AV fistula into the vein.

FIG. 1 illustrates the venous end 2 of an AV fistula 4 joined to a vein 6 at a junction 8. The opposite end of AV fistula 4 is connected to an artery 9. The construction of AV fistula 4 and the connections to artery 9 and vein 6 are conventional.

Figure 4:
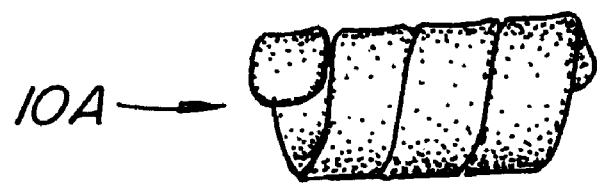
FIG. 4 illustrates a further alternative embodiment of the stent graft of FIG. 2 in which the turns are adjacent to one another.

To help treat and/or prevent the obstruction or blockage 6 at junction 8, an endoluminal prosthesis in the form of a coiled stent graft, such as stent graft 10, is placed so that it extends within the venous end 2 of AV fistula 4 and within vein 6 so that stent graft 10 spans both sides of junction 8. Stent graft 10 is typically of a type in which the turns 12 are generally evenly spaced apart from one another by gaps 14. While turns 12 of stent graft 10 may be evenly spaced when in a freely-expanded condition, as in FIG. 2, when placed within fistula 4 and vein 6, the gaps may not be the same from turn to turn. For example, FIG. 1 illustrates the situation in which gap 14A at junction 8 is somewhat larger than the other gaps 14. In some situations it may be desirable to use a stent graft 10A, shown in FIG. 4, in which the turns are adjacent to one another so that even at junction 8, turns 12 would be adjacent or closely spaced to effectively block fluid flow along vein 6 on one side of junction 8, that is the upstream (left) side in FIG. 1.

A typical AV fistula 4 has an inside diameter of about 4–10 mm and a length of about 2–10 cm. Stent graft 10 would typically have a slightly larger freely-expanded outside diameter such as 5 mm for a 4 mm diameter AV fistula. The length of stent graft 10 typically depends upon the length of the AV fistula and whether the stent graft is to extend into one or both of vein 6 and artery 9. Thus, the length of stent graft 10 may range from, for example, 1 cm to over 10 cm.

Figure 2:
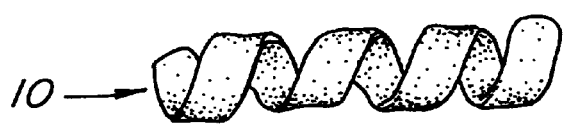
FIG. 2 illustrates the stent graft of FIG. 1 prior to placement into the AV fistula and vein.
Figure 3:
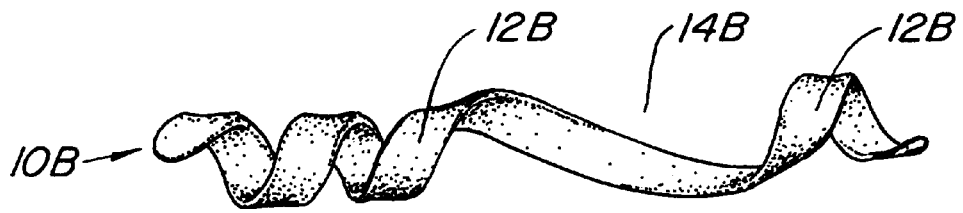
FIG. 3 illustrates an alternative embodiment of the stent graft of FIG. 2 in which the pitch between two adjacent turns is substantially greater than the pitch between other of the turns to help prevent restriction to fluid flow along the vein at the junction of the AV fistula.

Instead of the evenly spaced turns 12 of stent graft 10 of FIGS. 1 and 2, a stent graft 10B, see FIG. 3, could be used in which an extended gap 14B is provided between adjacent turns 12B. Stent graft 10B may find particular use with gap 14B positioned at junction 8 to help ensure minimal restriction to fluid flow along vein 6 as well as from AV fistula 4 into vein 6.

A stent graft, having three sections with closely-spaced turns at the end sections and one or more loosely-spaced turns at the intermediate section, may be used. This embodiment may be used, for example, with one end section within fistula 4, the intermediate section at junction 8 and the other end section within vein 6. In addition, while the stent graft is typically a unitary item, it may be desirable to make the stent graft from two or more stent graft segments. For example, the stent graft could include three relatively short stent graft segments, one for placement in AV fistula 4, one for placement at junction 8 and one for placement along vein 6.

In the preferred embodiments stent grafts 10, 10A and 10B are made by covering wire stent blanks 16 (see FIG. 5) with a suitable graft material 15, such as ePTFE Dacron® polyester, polyurethane or natural vein. Stent blank 16 may be made of, for example, a temperature sensitive, shape memory alloy which tends to assume a radially extended position when at body temperature. Other means for expanding stent graft 10, such as or the application of an electric current or other energy source to heat the stent, or the use of simple spring stents, may also be used.

Figure 5:
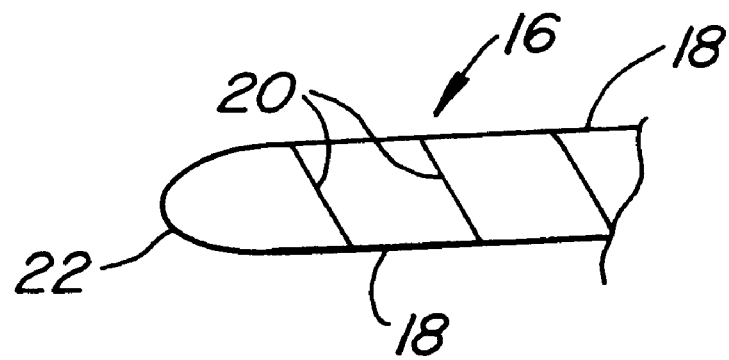
FIG. 5 illustrates the flattened of the stent graft of FIG. 2 with the graft material removed to illustrate the stent.
Figure 6:
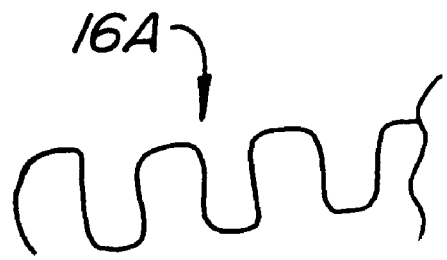
FIG. 6 illustrates an alternative embodiment of the stent of FIG. 5.

FIG. 5 illustrates one end of a stent blank 16, used to create stent grafts 10, 10A and 10B, prior to covering stent blank 16 with ePTFE graft material. Stent blank 16 comprises a pair of rails 18 connected by connectors 20, rails 18 being joined at their ends to form blunt ends 22. Blunt ends 22 are configured and constructed so to minimize trauma to patient tissue. Other types of stent structures may be used. For example, the angled connectors 20 of FIG. 5 could be replaced by one or more of perpendicular connecting elements, x-shaped connector elements, undulating connector elements or any of a variety of connector elements. Also, rails 18 could be discontinuous, which would occur, for example, when stent blank 16 is made of wire formed into a series of deep undulations, such as illustrated in FIG. 6. Other types of coiled stent structures made of a variety of biocompatible materials can be used as well. In the above-described preferred embodiments the entire stent blank is covered with graft material. In some situations it may not be necessary or desirable to cover the entire stent blank with graft material. Also, the stent blank may not have a constant width and the stent graft may have a diameter which changes over its length.

In use stent graft 10 may be placed into vein 6 when AV fistula 4 is initially grafted between the artery and vein. However, in the usual case stent graft 10 would not be used until the formation of some blockage at junction 8 has been observed. After any necessary removal of the blockage, stent graft 10 can be mounted to a suitable placement catheter, such as one disclosed in U.S. patent application Ser. No. 09/400,952 filed Sep. 22, 1999, and entitled "Catheter Assembly with Controlled Release Endoluminal Prosthesis". With stent graft 10 tightly wrapped about the placement catheter, the placement catheter is advanced percutaneously into vein 6, and then into venous end 2 of AV fistula 4. Proper longitudinal and rotary placement of stent graft 10 can be monitored using remote visualization techniques, which may or may not involve the use of radiopaque markers carried by the stent graft. Radiopaque markers, when used, would likely be used at the ends of stent graft 10 and/or at the turn or turns 12 expected to be at or adjacent to junction 8 to help ensure proper placement. Once in position, stent graft 10 is released from the placement catheter and is expanded to the position of FIG. 1.

To help eliminate any substantial hindrance to fluid flow along vein 6, stent graft 10 may be selected and placed so that the turns 12 at junction 8 are separated by a distance X. However, future testing may indicate that in some, or possibly all, cases it may be desirable to have turns 12 at junction 8 be positioned adjacent one another to eliminate gap 14A and thus prevent fluid flow through the vein on the upstream (left) side of the junction.

Other modification and variation can be made to the disclosed embodiments without departing from the subject of the invention as defined in the following claims. For example, stent 10 could be a bifurcated, generally Y-shaped stent graft.

Any and all patents, patent applications and printed publications referred to above are incorporated by reference.

What is claimed is:

1. A method for enhancing the finction of an AV fistula comprising:
   selecting an endoluminal prosthesis comprising a generally helically-extending coiled body and a graft material at least partly covering the coiled body to create a coiled stent graft with generally helically-extending turns, said turns having an average width;
   placing the stent graft within an AV fistula and within at least one blood vessel to which the AV fistula is connected, the placing step being carried out so the stent graft extends across the junction between the AV fistula and the at least one blood vessel; and
   the selecting and placing steps being carried out so that the turns of the stent graft at the junction are spaced-apart from one another so as to not block fluid flow through the blood vessel.

2. The method according to claim 1 wherein the placing step is carried out with the stent graft placed within the AV fistula and a vein.

3. A method for enhancing the function of an AV fistula comprising:
   selecting an endoluminal prosthesis comprising a generally helically-extending coiled body and a graft material at least partly covering the coiled body to create a coiled stent graft with generally helically-extending turns, said turns having an average width;
   placing the stent graft within an AV fistula and optionally within at least one blood vessel to which the AV fistula is connected;
   the placing step being carried out with the stent graft placed within the AV fistula and at least one blood vessel so the stent graft extends across the junction between the AV fistula and the at least one blood vessel; and
   the selecting and placing steps being carried out so that the turn of the stent graft at the junction are next to one another so to effectively block fluid flow along the blood vessel on one side of the junction.

4. A method for enhancing the function of an AV fistula comprising:

selecting an endoluminal prosthesis comprising a generally helically-extending coiled body and a graft material at least partly covering the coiled body to create a coiled stent graft with generally helically-extending turns;

placing the stent graft within the AV fistula and a vein so the stent graft extends across the junction between the AV fistula and the vein;

the selecting and placing steps being carried out so that the turns of the stent graft at the junction are separated by a gap so to not block fluid flow along the vein.

5. An AV fistula assembly comprising:

an artificial AV fistula comprising a tubular body having a venous end and arterial end;

a coiled stent graft comprising a generally helically-extending coiled body and a graft material at least partially covering the coiled body;

the coiled stent graft having generally helically-extending turns, said turns having edges;

at least some of the turns being spaced-apart by gaps so that said spaced-apart turns do not overlap one another, the lengths of the gaps varying by more than 100%; and the stent graft housable at least partially within the AV fistula at at least one of venous and arterial ends.

6. The assembly according to claim 5 wherein the graft material is synthetic graft material.

7. The assembly according to claim 6 wherein the synthetic graft material is expanded PTFE.

8. An AV fistula assembly comprising:

an artificial AV fistula comprising a tubular body having a venous end and arterial end;

a coiled stent graft comprising a generally helically-extending coiled body and a graft material at least partially covering the coiled body;

the coiled body comprising a framework of lateral rails and connectors;

the coiled stent graft having generally helically-extending turns, said turns having edges; and the stent graft housable at least partially within the AV fistula at at least one of venous and arterial ends.

9. An AV fistula assembly comprising:

an artificial AV fistula comprising a tubular body having a venous end an arterial end;

a coiled stent graft comprising a generally helically-extending coiled body and a graft material at least partially covering the coiled body, the turns of the coiled stent graft being generally helically-extending and spaced-apart by gaps;

the lengths of the gaps varying by more than 100%; and the stent graft housable partially within the AV fistula and extending past at least one of the venous and arterial ends.

* * * * *